United States Patent [19]

Gordon

[11] Patent Number: 4,504,226
[45] Date of Patent: Mar. 12, 1985

[54] METHOD AND APPARATUS FOR POSITIONING MAXILLARY AND MANDIBULAR ARCH MODELS FOR FORMING A GNATHOLOGICAL POSITIONER

[76] Inventor: Woodford W. Gordon, 125 Miraloma Dr., San Francisco, Calif. 94127

[21] Appl. No.: 359,377

[22] Filed: Mar. 18, 1982

[51] Int. Cl.³ .............................................. A61C 11/00
[52] U.S. Cl. ........................................ 433/63; 433/65
[58] Field of Search ...................... 433/56, 57, 58, 59, 433/61, 62, 63, 64, 65, 66, 67

[56] References Cited

U.S. PATENT DOCUMENTS

| 2,200,058 | 5/1940 | Chott | 433/65 X |
| 2,270,561 | 1/1942 | Sanborn | 433/63 |
| 2,423,522 | 7/1947 | Shmukler et al. | 433/65 X |
| 2,641,838 | 6/1953 | Beresin | 433/65 |
| 2,748,481 | 6/1956 | Glueck | 433/56 X |
| 3,414,977 | 12/1968 | Cayo | 433/57 |
| 4,402,670 | 9/1983 | Lee | 433/61 |

OTHER PUBLICATIONS

R. H. Roth, "Functional Occlusion for the Orthodontist", Part I, Journal of Clinical Orthodontics, vol. XV, #1, Jan. 1981.
R. H. Roth, et al, "Functional Occlusion for the Orthodontist", Part II, Journal of Clinical Orthodontics, vol. XV, #2, Feb. 1981.
R. H. Roth, "Functional Occlusion for the Orthodontist", Part III, Journal of Clinical Orthodontics, vol. XV, #3, Mar. 1981.
R. H. Roth, et al, "Functional Occlusion for the Orthodontist", Part IV, Journal of Clinical Orthodontics, vol. XV, #4, Apr. 1981.

Primary Examiner—Robert P. Swiatek
Attorney, Agent, or Firm—Fitch, Even, Tabin & Flannery

[57] ABSTRACT

Maxillary and mandibular arch models are positioned in an articulator so that the plane of occlusion is in a three dimensional relationship about the articulator hinge axis substantially corresponding to the three dimensional relationship of the intraoral plane of occlusion about the mandibular hinge axis. A mechanically adjustable guide plane element is substituted in the place of one of the arch models and adjusted to fit the plane of occlusion of the other arch model. The teeth of such model are then adjusted in accordance with the occlusal plane guide. The occlusal plane guide is replaced by the heretofore removed arch model and its teeth are brought into centric relation occlusion with the previously adjusted arch model. The arch models are then discluded to a preselected centric wedge of opening of which an impression is made. A gnathological positioner may be fabricated from this impression.

9 Claims, 7 Drawing Figures

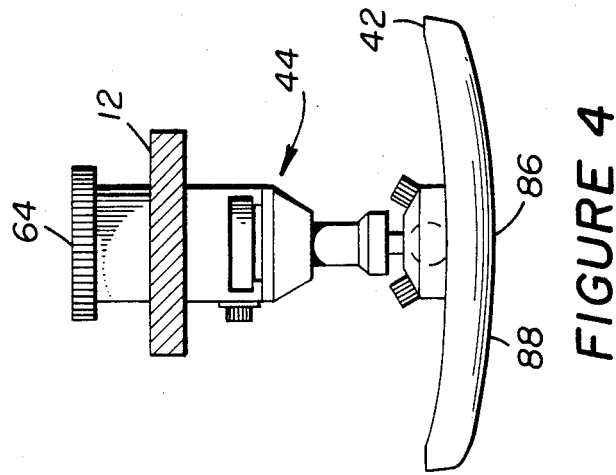
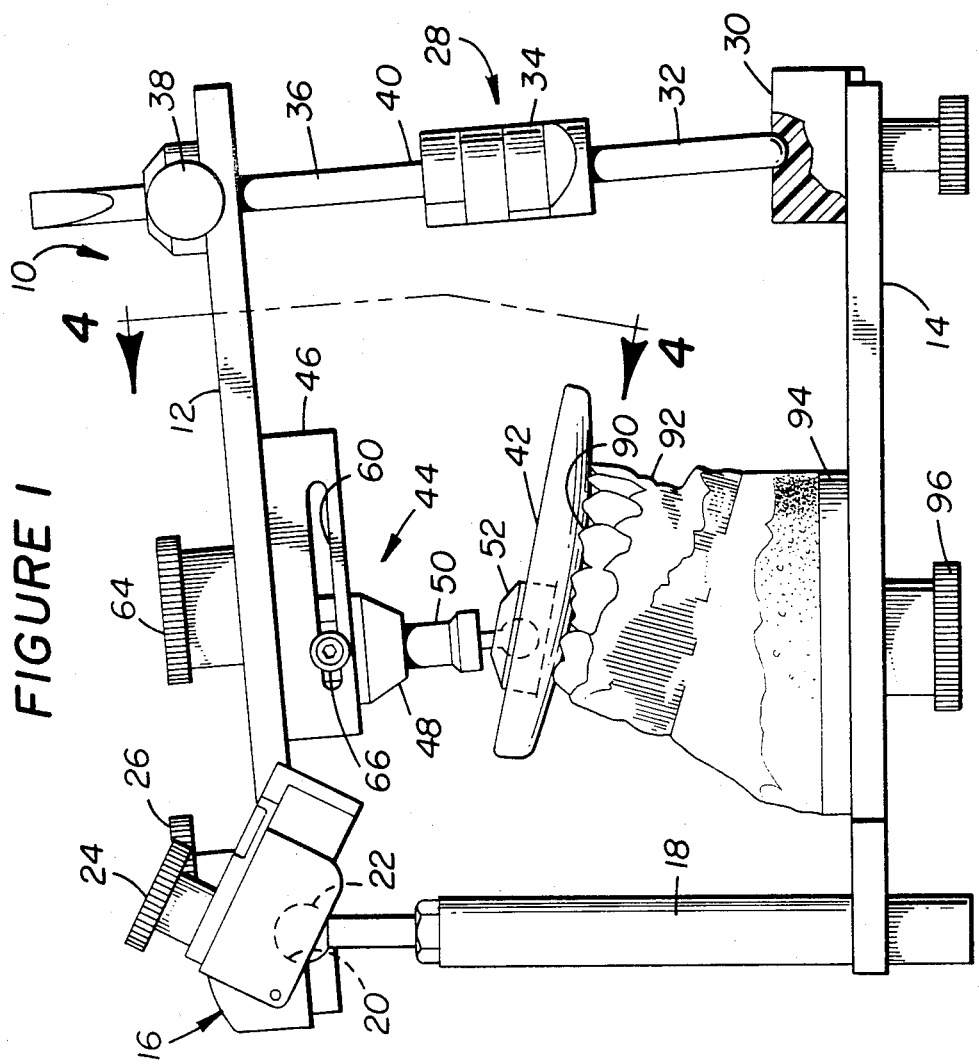

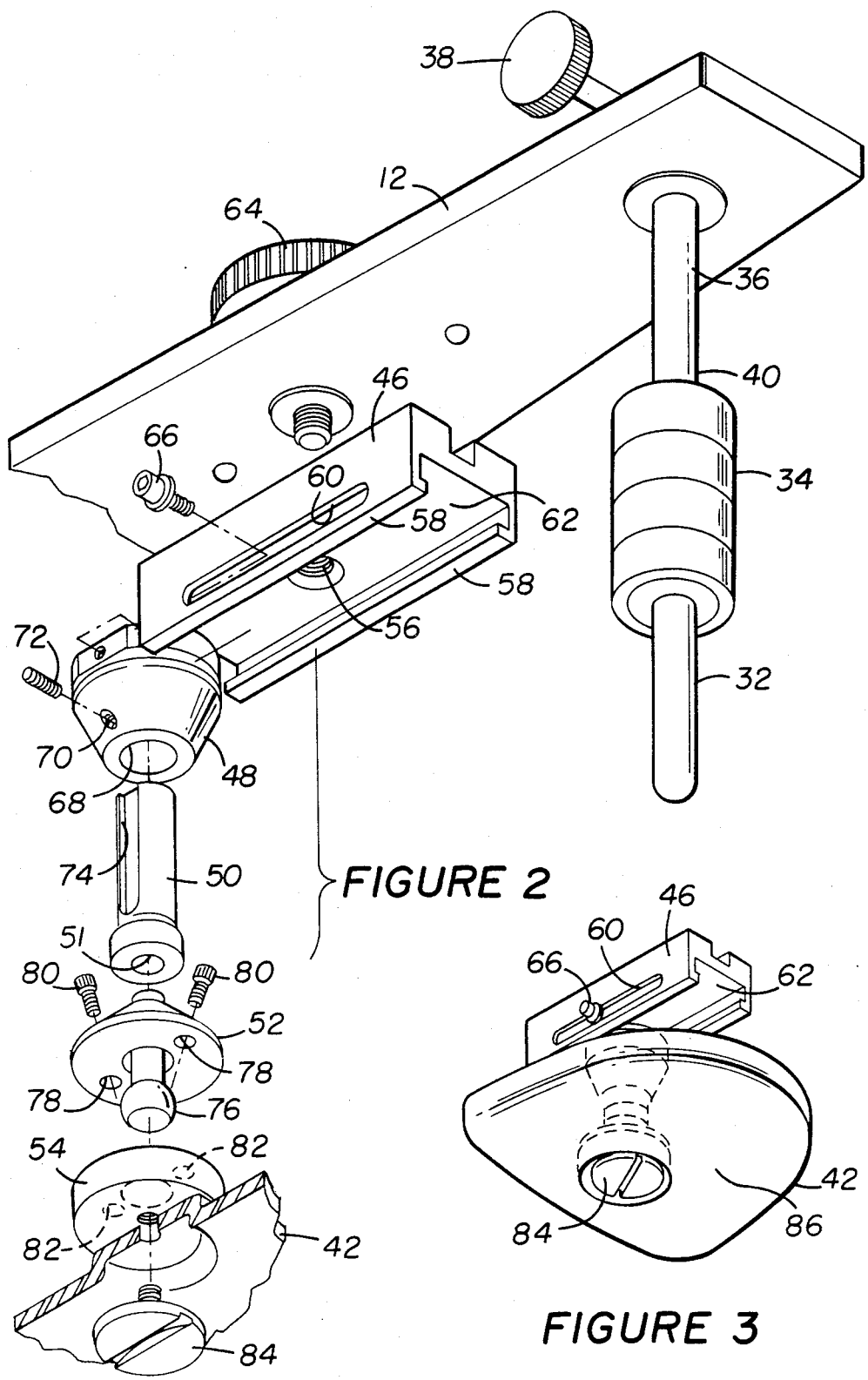

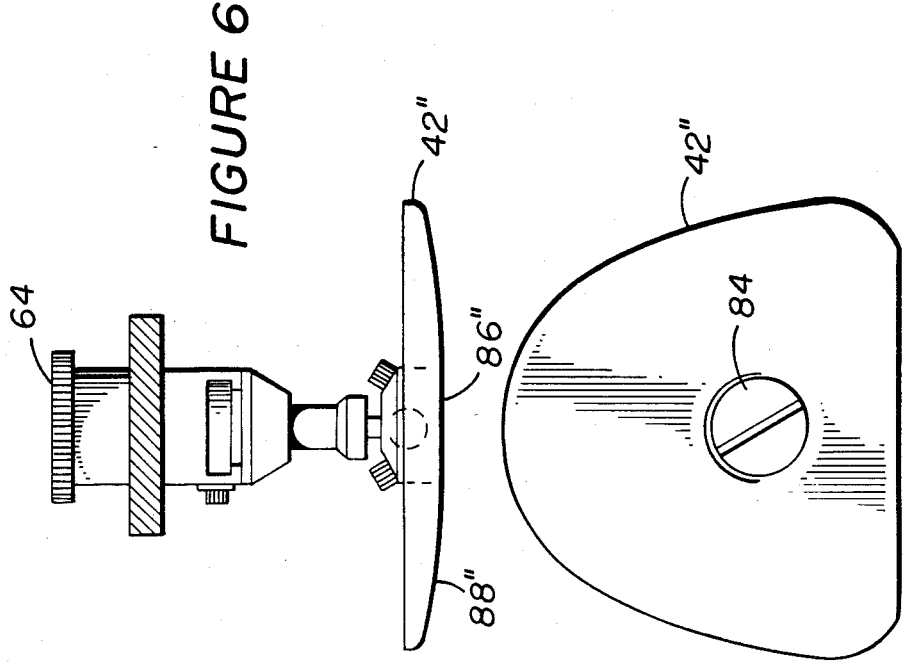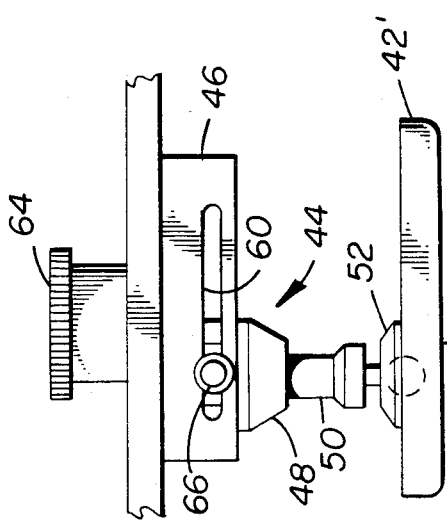

METHOD AND APPARATUS FOR POSITIONING MAXILLARY AND MANDIBULAR ARCH MODELS FOR FORMING A GNATHOLOGICAL POSITIONER

The present invention relates generally to a method and apparatus for accurately positioning maxillary and mandibular arch models in an articulator and more particularly to such a method and apparatus for accurately locating the plane of occlusion of the arch models relative to an axis of the articulator in discluding the arch models about the axes to a preselected discluded position to form an impression between each arch model in the discluded position so that an identical centric wedge of opening is achieved between the arch models as would occur intraorally in a patient. A gnathological positioner may be formed from the impression.

BACKGROUND OF THE INVENTION

Articulators have commonly been employed in the prior dental art as a gnathological setup technique for positioning maxillary (upper) and mandibular (lower) arch models in movable relation to each other between an occluded position and a position defining a centric wedge of opening corresponding to the wedge opening of a patient.

Most of the prior art setup techniques only require that one find centric occlusion by grinding a set of arch models on a model grinder while the teeth are fitted together with the teeth on the mandibular arch model being cut off and set up in wax. Some techniques set up half of the arch at a time in an effort to maintain the vertical height while others only remove some of the teeth from the arch. Usually the mandibular arch model is completed and then the maxillary teeth are removed from its arch model and set to occlude with the mandibular model set up using a well known table top orientation technique to establish the arch relation between the two models. When the setup is completed, the models are fixed in the articulator to create an arc opening similar to that of the patient. A positioner or other dental device may then be used based upon the setup and mounting achieved in the articulator.

Various other prior art techniques are available over and above the simple approach described above. However, all of the known prior art techniques have inherent limitations when transferring the centric wedge opening of the patient to the set of arch models mounted on the articulator.

One of these prior art methods accomplishes orientation of the mandibular arch model on the articulator by measuring the angle of the mandible from the condyles to the tip of the incisors, the angle taken from a two-dimensional head plate which superimposes both the condyles as well as the lower incisors and molars. The two-dimentional basis of the head plate makes it difficult and unlikely to accurately capture the three-dimensional position of the plane of occlusion for the models relative to the condyles and the mandibular hinge axis definded by the condyles. The method described immediately hereinabove does not find an accurate relationship of the maxillary to the cranial base or the mandibular relation to the maxillar. Similarly, this technique does not establish the centric wedge of opening corresponding to that of the patient with the condyles being seated in the superior position within the fossae. A gnathological positioner produced using this prior art method and used by the patient for an extended period of time causes the patient to subluxate the condyles and extend them forwardly in order to seat his teeth in the gnathological positioner. This condition may cause temporomandibular joint (TMJ) problems, such as pain, dysfunction, adverse tooth movement and trauma, centric slides, and a breakdown of the periodontal membranes.

Accordingly, there has been found to remain a particular need for a method and apparatus for accurately positioning the maxillary and mandibular arch models in the articulator with the plane of occlusion mounted relative to the axes of the articulator in three dimensional simulation of the same intraoral relationship for the patient.

SUMMARY OF THE INVENTION

Accordingly, it is an object of the present invention to overcome the problems and limitations of the above described prior art. It is a further object of the present invention to provide a novel and improved method and apparatus for accurately mounting maxillary and mandibular arch models in an articulator.

It is yet a further object of the present invention to provide such a method and apparatus for mounting the arch models in an articulator in a three dimensional relationship about an axis defined by the articulator substantially corresponding to the three dimensional relationship of a maxillary arch and a mandibular arch of the patient about a mandibular hinge axis.

It is still another object of the present invention to provide such a method and apparatus for locating one of the arch models on the articulator with respect to a predetermined centric wedge of opening corresponding to the centric wedge of opening occurring intraorally in the patient.

According to the present invention, the maxillary arch models and the mandibular arch models are mounted in the articulator in a three dimensional relationhip about an axis defined by the articulator which substantially corresponds to the three dimensional relationship of the maxillary arch and a mandibular arch of the patient about the mandibular hinge axis. Selected teeth of each arch model are intruded to eliminate vertical discrepancy between centric relation and centric occlusion. Each tooth of one of the arch models is then set to a predetermined plane of occlusion. The teeth of the other model are then set into centric relation occlusion with the other arch model. The arch models are then discluded to a preselected centric wedge of opening of which an impression is made. A gnathological positioner may be fabricated from this impression.

The improved apparatus of the present invention includes an occlusal guide plane detachably mounted to a first mounting portion of the articulator in place of one said arch models. The occlusal guide plane is mechanically adjustable, and is positioned against the other remaining arch model in the articulator such that the teeth in said remaining arch model can be positioned with respect to the plane of occlusion.

BRIEF DESCRIPTION OF THE DRAWINGS

FIG. 1 is a side view in elevation of an articulator including the apparatus of the present invention and suitable for practicing the method of the invention;

FIG. 2 is an exploded perspective view of the apparatus of the present invention of FIG. 1 and suitable for practicing the method and apparatus of the present invention;

FIG. 3 is a fragmentary view illustrating the assembled relation of the components of the occlusal guide plane of FIG. 2;

FIG. 4 is a fragmentary view, with parts in section, taken along line 4—4 of FIG. 1, FIGS. 1 and 4 illustrating together the configuration of a plane of occlusion for an occlusal guide plane;

FIG. 5 is a fragmentary view of a portion of the articulator of FIG. 1, illustrating a variation of the occlusal guide plane of FIGS. 1 and 4;

FIG. 6 is similarly a fragmentary view as in FIG. 5 illustrating yet another variation of the occlusal guide plane of FIGS. 1 and 4; and FIG. 7 is a bottom view of the occlusal guide plane of FIG. 6.

DETAILED DESCRIPTION OF THE DRAWINGS

In the following description, the components of a conventional articulator are first described followed by description of a variety of novel occlusal plane guides provided by the present invention and novel means for mounting any one of the occlusal plane guides to be selectively positioned in the articulator. The method of the invention is then described with reference to the apparatus of FIGS. 1-7.

The conventional articulator, which is hereinafter described in as much detail to understand the principles of the present invention, is commercially available from Denar Corporation under the model designation Denar Mark II.

Referring now to FIG. 1, an articulator 10 includes a generally longitudinal first mounting portion 12, a second mounting portion 14, a condyle housing 16, and a condyle post 18. Condyle housing 16 has an internal socket 20. Condyle post 18 has a condyle head 22 received by socket 20. Condyle housing 16 further has a Bennet adjustment 24 and an eminence adjustment 26.

Articulator 10 includes a scaler adjustment 28 having incisor guide table 30, a shaft 32, a micrometer adjustment unit 34, an incisor guide pin 36, an incisor guide pin lock 38, and a calibration scale 40.

In accordance with the prior art, first mounting portion 12 is in a hinged relationship with second mounting portion 14, the condyle housing 16 and condyle head 22 being operative to simulate the movement of the condyles in the fossa in a patient. Scaler adjustment 28 allows, as hereinafter described, the orthodontist to measure with a maxillary arch model and a mandibular arch model a vertical discrepency between centric relation, being the measurement of initial contact between each model, and centric occlusion, being the measurement when all teeth of each model fit together.

The novel improvement of the articulator 10 includes an occlusal plane guide 42 and means 44 for detachably mounting occlusal plane guide 42 to first mounting portion 12 and for selectively positioning occlusal plane guide 42 between first and second mounting portions 12 and 14. Heretofore in the prior art, the common practice was to affix the occlusal plane guide 42 to first mounting portion 12 with plaster. This does not permit any adjustment or "fine tuning" of the plane of occlusion defined by occlusal plane guide 42. Referring also to FIGS. 2 and 3, mounting means 44 includes the longitudinal frame 46, a chuck 48, a pin 50, a housing 52, and a base member 54.

Longitudinal frame 46 has a threaded opening 56 disposed through the top portion thereof, a pair of inwardly facing L-shaped members 58 disposed longitudinally along its lower edge portions on opposite sides, and a longitudinal slot 60 formed through one of L-shaped members 58. L-shaped members 58 define a raceway 62, slot 60 being in communication with raceway 62. First mounting portion 12 has a knurled mounting bolt 64 which threadably engages threaded opening 56.

An upper portion of chuck 48 is dimensioned to be received by raceway 62 and supported in linear slidable engagement by L-shaped members 58 and has an Allan head bolt 66 threadably engaged thereto. Bolt 66 is received through slot 60 and engages frame 46 to secure chuck 48 in a selected horizontal position longitudinally with respect to first mounting portion 12. A lower portion of chuck 48 has an axial bore 68, a threaded opening 70 and a set screw 72. Threaded opening 70 communicates radially with axial bore 68 and threadedly receives set screw 72.

Pin 50 is dimensioned to be coaxially received by axial bore 68 and has an axially disposed keyway 74. Set screw 72 engages keyway 74 preventing pin 50 from rotating within axial bore 68 and further vertically locks pin 50 to select the vertical position of pin 50. Pin 50 also includes a coaxial bore 51 formed therein.

Housing 52 is suspended from pin 50 and has a ball pin 76 projecting downwardly in coaxial alignment with pin 50, a pair of threaded openings 78, and a pair of adjustment bolts 80, each bolt 80 threadedly received by one of the openings 78. Ball pin 76 is force fit or otherwise securely retained in a conventional manner on bore 51 of pin 50.

Base member 54 is adapted to receive ball pin 76 and has threaded openings 82. Each opening 82 threadedly receives one of adjustment bolts 80 to secure base member 54 to housing 52 and further permit angular adjustment of base member 54 about ball pin 76. Base member 54 further has a mounting screw 84 which secures occlusal guide plane 42 thereto.

Thus, occlusal guide plane 42 may be selectively positioned between first and second mounting members 12 and 14, horizontally by adjustment of chuck 48 in frame 46, vertically by adjustment of pin 50 in chuck 48, and angularly by adjustment of base member 54 about ball pin 76, all as hereinabove described.

Referring also to FIG. 4 and again to FIG. 1, occlusal guide plane 42 has a lower surface 86 which defines a plane of occlusion. As best seen in FIG. 4, lower surface 86 has a curved portion 88 of about 17 degrees, indicating a curve of Wilson. As best seen in FIG. 1, lower surface 86 further has a curved portion 90 with a depth of about 2 millimeters along the mesiodistal dimension corresponding to the bicuspid area, indicating a curve of Spee.

Referring now to FIG. 5, there is shown another embodiment of an occlusal guide plane 42'. Occlusal guide plane 42' is secured by mounting means 44 to first mounting portion 12 as hereinabove described. Occlusal guide plane 42' has a lower surface 86' defining a plane of occlusion which is substantially flat. Occlusal guide plane 42' does not have any lateral or mesiodistal curvature.

Referring now to FIGS. 6 and 7, there is shown yet another embodiment of an occlusal guide plane 42".

Occlusal guide plane 42" is secured by mounting means 44 to first mounting portion 12 as hereinabove described. Occlusal guide plane 42" has a lower surface 86" which has a curved portion 88" which is the curve of Wilson hereinabove described. However, lower surface 86" has substantially zero mesiodistal curvature, or no curve of Spee.

The apparatus of the present invention has been described hereinabove in detail. Although it is believed to be apparent to one skilled in the art to practice the method of the invention from the herinabove apparatus description, the method of the invention is set forth in detail to permit a full teaching of the invention.

In the method, maxillary and mandibular arch models are prepared from the patient along with a centrically related interocclusal bite or wax record while the condyles are seated in their most superior (highest centric related) position. In treating of the patient, this superior centric relation for the condyles is established in a prior procedure, for example, by means of a repositioning splint. It is contemplated in practicing the method of the present invention, that the patient has undergone prior orthodontic procedures such as repositioning of the mandibule so that the condyles are properly seated in the fossa, and prior repositioning of the teeth by other appliances, for example by banding.

The maxillary and mandibular arch models are mounted on the articulator with the plane of occlusion located relative to the hinge axis of the articulator and corresponding dimensionally to the intraoral plane of occlusion relative to the mandibular hinge axis. Two methods for locating the plane of occlusion relative to the hinge axis are described in greater detail hereinbelow.

After the maxillary and mandibular arch models are properly positioned, one of the models is removed and in its place is positioned the occlusal guide plane. With the occlusal guide plane properly positioned in the articulator, the teeth of the other model are then placed in accurate engagement with the occlusal guide plane. Thus, the teeth on the model are adjusted in accordance with conventional dental laboratory techniques to determine their preferred orientation while maintaining the plane of occlusion with the occlusal guide plane. Thereafter, the occlusal guide plane is replaced by the arch model heretofore removed which is then properly mounted upon the articulator in an occluded relation with the adjusted arch model. The teeth of the replaced arch model are then individually adjusted to occlude with the teeth of the adjusted arch model.

The arch models are then discluded to form a centric wedge of opening closely simulating that which occurs intraorally in the patient. An impression is taken of this wedge opening, from which a gnathological positioner may be fabricated.

Describing the method of the invention in greater detail, maxillary and a mandibular arch models are formed by conventional techniques. At the same time, a conventional interocclusal wax record is taken of the patient to precisely identify a condition of occlusion between the maxillary and mandibular arch models.

The invention then contemplates one of two methods for three dimensionally locating the patient's mandibular hinge axis relative to the plane of occlusion. The first method is termed an ideal or "true hinge axis technique" which requires a pantographic recording of the patient's mandibular jaw movements. A centrically related interocclusal wax record is taken with the patient's condyles being seated in their most superior or highest position relative to the fossae. The maxillary model is seated in the clutch of the pantograph with the mandibular model then being mounted to the maxillary model by means of the interocclusal wax record to permit a fully adjustable anatomical arc on the articulator. The pantograph thus establishes an ideal location of the occlusal guide plane upon the articulator so that a plane of occlusion is accurately located relative to the hinge axis of the articulator in ideal simulation to intraoral conditions of the patient. This ideal "true hinge axis technique" is preferrably employed if the patient has had a past history of temporal mandibular joint problems or has exhibited excessive movement upon use of a repositioning splint. The use and construction of the pantograph are well known in the art.

The second method for three dimensionally locating the patient mandibular hinge axis relative to the plane of occlusion is termed a practical or "estimated hinge axis technique" which is less time consuming in the orthodontic office and employs a conventional facebow transfer. The maxillary and mandibular models and the centrically related interocclusal wax record are formed as hereinabove described. The maxillary and mandibular arch models are then mounted to a semi-adjustable arc on the articulator by mounting the facebow to the articulator with a bite fork registration, all by known orthodontic techniques. This practical method may be used on most orthodontic patients who show no signs of side shift, temporal mandibular joint problems or excessive movement upon use of a repositioning splint.

Once the plane of occlusion of the patient has been accurately three dimensionally located relative to the mandibular hinge axis, the maxillary arch model is mounted to articulator 10 of FIG. 1 maintaining the plane of occlusion properly located relative to the hinge axis of articulator 10. The maxillary arch model (not shown) is mounted to first mounting portion 12. A mandibular arch model 92 is shown in FIG. 1 mounted to second mounting portion 14. Arch model 92 includes a mounting plate 94 upon which the arch model is constructed. Second mounting portion 14 further has a knurled nut 96 which threadedly engages mounting plate 94.

The maxillary arch model having been accurately positioned, the mandibular arch model is positioned to occlude thereto by means of the centric related interocclusal wax record. Note that to fabricate a gnathological tooth positioner using this method, the occlusal plane must be kept fixed with respect to the hinge axis during the set up process in order to capture the true arc or wedge of upper and lower teeth.

Thus, a duplicate set of maxillary and mandibular arch models is required in addition to the heretofore mounted models. The duplicate models are sectioned and wedged, and placed into, for example, a Bioplast mold. A layer of wax is poured over the teeth and a stone base poured over the wax base that the teeth are set into. This creates a duplicate set of maxillary and mandibular arch models, but with the teeth now set in wax. These duplicate models (hereinafter referred to as wax models) are then transferred to articulator 10 by utilizing the centric registration that the original models were mounted from.

First, the mandibular wax model is mounted into centric registration with the maxillary solid model still in place on articulator 10. After the mandibular wax model has been mounted, the maxillary wax model is mounted to the centric registration, providing a duplicate set of models with the teeth set in wax mounted to articulator 10 exactly in the same position as the original mountings. The original models may be saved for a permanent record of the case.

After the maxillary and mandibular wax models have been transferred to articulator 10, a centric pin discrepancy between centric relation and centric occlusion is calculated. Incisor guide pin 36 is raised half the amount of the centric relation-centric occlusion vertical discrepancy, as measured by micrometer adjustment unit 34 and calibration scale 40. The mandibular wax model is placed under a heat lamp until the wax in which the teeth are mounted is uniformly softened, the model then being placed back on articulator 10 and articulator 10 closed. Closing of articulator 10 intrudes the teeth on the mandibular arch model that are responsible for the centric vertical discrepancy, but intrudes them only half the distance of the discrepancy. Incisor guide pin 36 is then set at the centric occlusion reading and the maxillary wax model is heated under a heat lamp. The maxillary wax model is placed back on articulator 10 and the other half of the centric vertical discrepancy is eliminated by hinging the articulator 10 to the closed position until incisor guide pin 36 rests upon incisor guide table 30. Thus, the vertical discrepancy between centric relation and centric occlusion has been eliminated while simultaneously maintaining the plane of occlusion in the exact position it had heretofore been set relative to the hinge axis of articulator 10.

The maxillary wax model is now removed from articulator 10 and in its place mounting means 44 is secured to upper mounting portion 12 as hereinabove described. One of occlusal guide planes 42, 42', 42" is mechanically adjusted, as hereinabove described, to obtain the best fit against the occlusal plane of the mandibular wax model. In obtaining the best fit, the cuspids of the mandibular wax model should either be removed from the arch or intruded.

The teeth of the mandibular wax model are then brought into contact with occlusal guide plane 42, 42', 42" While the rotations of each tooth are corrected, the posterior teeth are moved forward into a space left by previous banding, and the anterior teeth are moved back into such bandspace. Furthermore, any width discrepancy can be correct at this time. For instance, if there is a discrepancy between maxillary and mandibular molar widths of one millimeter in centric relation, the mandibular molar can be set buccally one half millimeter. When the maxillary teeth are set to the mandibulars they will automatically be brought lingually one ·half millimeter. The mandibular teeth are set against occlusal guide plane 42, 42', 42" until all the cusps of such teeth touch occlusal guide plane 42, 42', 42" in the molar area and until the marginal ridge heights are equal.

Once the mandibular wax model has been completely set to occlusal guide plane 42, 42', 42" the maxillary wax model is heated under a heat lamp until the wax has been softened uniformly. Occlusal guide plane 42, 42', 42" and mounting means 44 are removed from upper mounting portion 12 and the heated maxillary wax model placed back on first mounting portion 12. The maxillary wax model is then brought down into occlusion with the mandibular wax model. The teeth of the maxillary wax model are brought into centric relation occlusion with the teeth of the mandibular wax model. The articulator is then moved into excursions, and the anterior teeth are adjusted so as to produce an ideal anterior guidance so that a mutually protected occlusal scheme is obtained.

This mutually protected occlusal scheme is set into, as is known in the art, a Class 1 buccal segment relationship in centric relation. On excursions, the posterior teeth will exhibit clearance, while the anterior teeth will provide gentle guiding inclines that will gently disclude the posterior teeth on any excursive movement. The cuspids will provide the main guidance upon lateral movement.

In the protrusive excursion, the six maxillary anterior teeth contact the six mandibular anterior teeth equally and evenly in a gentle disclusive path while the maxillary cuspids ride against the mandibular first bicuspids during protrusive movement.

After completion of the above steps, incisor guide pin 36 is raised an appropriate amount to provide a wedge opening corresponding to the thickness of material required for a gnathological positioner. A centric registration of the setup with the wedge opening is made and impressions are taken of the maxillary and mandibular wax models of such setup. These impressions are poured in stone to create a duplicate set of stone models which are trimmed with the bases tapered to leave no undercut areas.

The mandibular stone model is arabitratily mounted to a lower member of a device known as a centric correlator, as disclosed in U.S. Pat. No. 4,184,225, issued Jan. 22, 1980 to Woodford W. Gordon, the applicant of the present invention. The teachings of such patent and the steps thereof necessary in practicing the present invention are hereby incorporated by reference as if set forth fully at this point. However, such steps as may be necessary to understand the present invention are summarized hereinbelow.

The wax impression taken from the wax models is set on the mandibular stone model mounted to the lower member of the centric correlator. Mounting plaster is placed on the maxillary stone model and the correlator is bolted closed before the mounting plaster reaches its initial set. This will capture the centric wedge of opening between the maxillary and mandibular models, as it exists on the articulator and as it exists in the patient's mouth.

After the plaster has set, the wax impression is removed and material known as Oralastic II, commercially available from Oral Arts Orthodontic Laboratory, Inc., Burlingame, California, is packed between the models. The material is placed between the maxillary and mandibular teeth on the correlator and the correlator is closed and bolted shut. When bolted shut, the correlator will index exactly back into centric relation as is described in the hereinabove incorporated reference.

After the material is compressed between the maxillary and mandibular teeth, a polyethylene strip can be used to press the labial surface of the material against the teeth. Excess material is trimmed and the packing process is completed. Curing of the material is accomplished by placing the entire correlator with the packed material into a pot of boiling water for 45 minutes. The correlator is then opened and the gnathological positioner formed from the cured material may be removed.

The finished gnathological positioner may be placed back onto the setup on articulator 10 to verify that the same three dimensional relationship is obtained with the gnathological positioner as was obtained with the wax registration of the centric wedge of opening.

It is thus readily apparent that there has been provided a method and apparatus for accurately positioning maxillary and mandibular arch models for forming a gnathological positioner.

It will be obvious that numerous modifications and variations are possible for the above described method and apparatus within the scope of the present invention. The foregoing deecription, setting forth various constructional and operational details for purposes of understanding only, is not to be taken as limiting the scope of the present invention which is defined only by the following claims.

What is claimed is:

1. A method of positioning a maxillary arch model and a mandibular arch model with respect to each other for forming a gnathological positioner, said method comprising the steps of:
   mounting said maxillary arch model and said mandibular arch model in an articulator in a three dimensional orientation about an articulator axis substantially corresponding to the three dimensional orientation of the maxillary arch and mandibular arch of a patient about a mandibular hinge axis;
   intruding selected teeth of each arch model to eliminate any vertical discrepancy between centric relation and centric occlusion;
   removing one of said maxillary arch model and said mandibular arch model from said articulator;
   mounting a mechanically adjustable occlusal guide plane to said articulator;
   three demensionally adjusting said occlusal guide plane to the plane of occlusion of the other of said maxillary arch model and said mandibular arch model mounted on said articulator;
   adjusting each tooth of said other model against said occlusal guide plane;
   removing said occlusal guide plane from said articulator;
   remounting said one arch model on said articulator;
   setting each tooth of said one arch model into centric relation occlusion with said other arch model;
   discluding rotationally about said articulator axis said maxillary arch model and said mandibular arch model to a selected discluded position; and
   forming an impression between each model in said discluded position.

2. A method as set forth in claim 1 further comprising steps of:
   forming said gnathological positioner from said impression.

3. A method as set forth in claim 1 wherein said mounting step includes:
   three dimensionally locating an intraoral plane of occlusion relative to said mandibular hinge axis;
   referencing said plane of occlusion in said articulator about said articulator axis;
   mounting a maxillary solid model to said articulator in centric relation to said plane of occlusion;
   mounting a mandibular solid model to said articulator in centric relation to said maxillary solid model;
   replacing said maxillary solid model with said maxillary arch model and placing said maxillary arch model in centric relation with said mandibular solid model;
   replacing said mandibular solid model with said mandibular arch model in centric relation with said maxillary arch model, the teeth of each of said maxillary arch model and said mandibular arch model being set in wax.

4. A method as set forth in claim 1 wherein said intruding step includes steps of:
   obtaining a guide pin measurement of said articulator when each arch model is in centric relation;
   obtaining a guide pin reading of said articulator when each model is in centric occlusion;
   adjusting said guide pin to a measurement intermediate each measurement obtained for centric relation and centric occlusion;
   heating a selected one of said maxillary arch model and said mandibular arch model, the teeth of said selected one being mounted in a heat sensitive material;
   closing said articulator until said guide pin rests against a guide pin table;
   adjusting said guide pin to the measurement obtained for centric occlusion;
   heating the other of said maxillary arch model and said mandibular arch model, the teeth of said other being set in a heat responsive material; and
   closing said articulator until said guide pin rests against said guide pin table.

5. In an articulator having a first mounting portion, a second mounting portion, and means for hingedly securing said first portion to said second portion in a spaced apart relationship, the improvement comprising:
   an occlusal guide plane; and
   means for detachably mounting said occlusal guide plane to one of said first mounting portion and said second mounting portion and for selectively positioning said occlusal guide plane between said first portion and said second portion, the other of said first portion and said second portion having an arch model mounted thereto, said occlusal guide plane being three dimensionally adjustable to a plane of occlusion of said arch model such that it is capable of horizontal and vertical sliding movement and angular rotation relative to said first and second mounting portions.

6. An articulator as set forth in claim 5 wherein said occlusal guide plane has a lower surface, said lower surface being substantially flat.

7. An articulator as set forth in claim 5 wherein said occlusal guide plane has a lower surface, said lower surface having a curve of Wilson.

8. An articulator as set forth in claim 5 wherein said occlusal guide plane has a lower surface, said lower surface having a curve of Wilson and a curve of Spee.

9. In an articulator having a first mounting portion, a second mounting portion, and means for hingedly securing said first portion to said second portion in a spaced apart relationship, the improvement comprising:
   an occlusal guide plane; and
   means for detachably mounting said occlusal guide plane to one of said first mounting portion and said second mounting portion and for selectively positioning said occlusal guide plane between said first portion and said second portion, the other of said first portion and said second portion having an arch model mounted thereto, said occlusal guide plane being adjustable to a plane of occlusion of said arch model, said mounting means including:
   a frame member having a raceway being mounted to said selected one of said first portion and said second portion;

a chuck having a top portion, a bottom portion and an axial bore disposed in said bottom portion, said top portion being supported in said raceway in linear slideable engagement;

a pin coaxially mounted in said axial bore and axially adjustable perpendicularly to said raceway;

a ball pin affixed to said pin and projecting outwardly and in coaxial alignment with said axial bore; and a base member rotationally mounted on said ball pin, said occlusal guide plane being mounted to said base member.

* * * * *